US00PP30735P2

(12) United States Plant Patent
Bourne

(10) Patent No.: US PP30,735 P2
(45) Date of Patent: Jul. 23, 2019

(54) GRAPEVINE NAMED 'SV30-13-10'

(50) Latin Name: *Vitis vinifera*
Varietal Denomination: SV30-13-10

(71) Applicant: Sunview Vineyards of California, Inc., Delano, CA (US)

(72) Inventor: Timothy F. Bourne, Visalia, CA (US)

(73) Assignee: Sunview Vineyards of California, Inc., Delano, CA (US)

( * ) Notice: Subject to any disclaimer, the term of this patent is extended or adjusted under 35 U.S.C. 154(b) by 0 days.

(21) Appl. No.: 16/350,140

(22) Filed: Oct. 2, 2018

(51) Int. Cl.
*A01H 5/08* (2018.01)
*A01H 6/88* (2018.01)

(52) U.S. Cl.
USPC ..... Plt./205

(58) Field of Classification Search
USPC ..... Plt./205
CPC ..... A01H 5/08; A01H 6/88
See application file for complete search history.

*Primary Examiner* — Annette H Para
(74) *Attorney, Agent, or Firm* — Baker Manock & Jensen PC; Eric C. Cole

(57) ABSTRACT

A new and distinct variety of grapevine plant named 'SV30-13-10' particularly characterized by its ellipsoidal to ovate shaped, seedless, red skinned berries which are medium-large, sweet, with a fruity *Vitis labrusca* flavor and which have tender texture. Productivity is high, with spur pruning only needed for a full crop.

2 Drawing Sheets

Latin name of the genus and species of the plant claimed: The plant claimed relates to a new and distinct variety of *Vitis vinifera*.

Variety denomination: The plant claimed shall be known as 'SV30-13-10'.

STATEMENT OF ANY FEDERALLY-SPONSORED RESEARCH AND DEVELOPMENT

The present invention is not subject of Federally-sponsored research or development.

BACKGROUND OF THE INVENTION

The present invention comprises a new and distinct cultivar of grapevine botanically known as *Vitis vinifera* and hereinafter referred to as grapevine named 'SV30-13-10'. As used herein, 'grapevine' refers to all plant parts including, vines, canes, tendrils, leaves, fruit and roots of 'SV30-13-10'. Grapevine named 'SV30-13-10' is the result of an effort to produce a red, seedless table grape with fruit characteristics superior to currently available red skinned grape cultivar 'Scarlet Royal' (U.S. Plant Pat. No. 16,229). This new cultivar originated from a cross conducted in May 2009 near McFarland, Calif. between grapevine plant selection 'SV16-72-83' (unpatented) and pollen parent 'SV21-66-158' (U.S. Plant Pat. No. 24,510). Resultant ovules from the cross were harvested 42 days after pollination and cultured on 'McCown's Woody Plant Medium' at a temperature of 22° C. for twelve weeks. Subsequently, the resultant embryonic plants were cultured in the same medium in the laboratory under twelve hours of light from standard fluorescent lamps at 26.4° C. The seedlings from this effort were transplanted to the greenhouse in October of 2010 and grown in the greenhouse at 26.4° C. with 12 hours' illumination under high pressure sodium vapor lamps. The seedling population of 315 plants was planted in the field in the spring of 2010 near Delano, Calif. The new grapevine was selected from this seedling population on Jul. 11, 2012. It was then propagated by cuttings and bench grafted to 'Freedom' (unpatented) rootstock in 2013. The present invention has been found to retain its distinctive characteristics through two successive asexual propagations.

Grapevine named 'SV30-13-10' differs from the female parent grapevine 'SV16-72-83' (unpatented) in that grapevine named 'SV30-13-10' has ovate shaped, dark red to black skinned, seedless berries, whereas 'SV16-72-83' (unpatented) has ovate shaped, black skinned berries with partially lignified seed traces and some epidermal reticulation.

Grapevine named 'SV30-13-10' differs from its male parent 'SV21-66-158' (U.S. Plant Pat. No. 24,510) in that grapevine named 'SV30-13-10' has dark red to black skinned berries while 'SV21-66-158' (U.S. Plant Pat. No. 24,510) has green skinned berries.

Grapevine named 'SV30-13-10' differs from the commercial cultivar 'Scarlet Royal' (U.S. Plant Pat. No. 16,229) in that grapevine named 'SV30-13-10' produces berries with no astringent flavour whereas 'Scarlet Royal' (U.S. Plant Pat. No. 16,229) produces berries at full ripeness which are astringent. Additionally, grapevine named 'SV30-13-10' produces berries which are very glossy/shiny due to absence of translucent, waxy bloom.

SUMMARY OF THE INVENTION

The following are the most outstanding and distinguishing characteristics of the ripe fruit of this new variety when grown under normal horticultural practices near McFarland, Calif. Some of the characteristics may vary depending upon changes in crop load and change of location of cultivation.

1. Dark red to black skinned fruit;
2. Very firm berry texture;

3. Large, ovate shaped berries with mild, sweet flavor; and
4. Berries which lack the typical translucent layer of wax found on grapes at maturity and which are very shiny in appearance.

BRIEF DESCRIPTION OF THE DRAWINGS

This new grapevine is illustrated by the accompanying photographs which show fruit clusters, leaves, canes, and tendrils. The colors shown are as true as can be reasonably obtained by conventional photographic procedures. The photographs were taken in 2012 on the seedling vine and in 2018 from a plant about 5 years-old, grown in a field near McFarland, Calif.

DETAILED BOTANICAL DESCRIPTION

Figure 1:
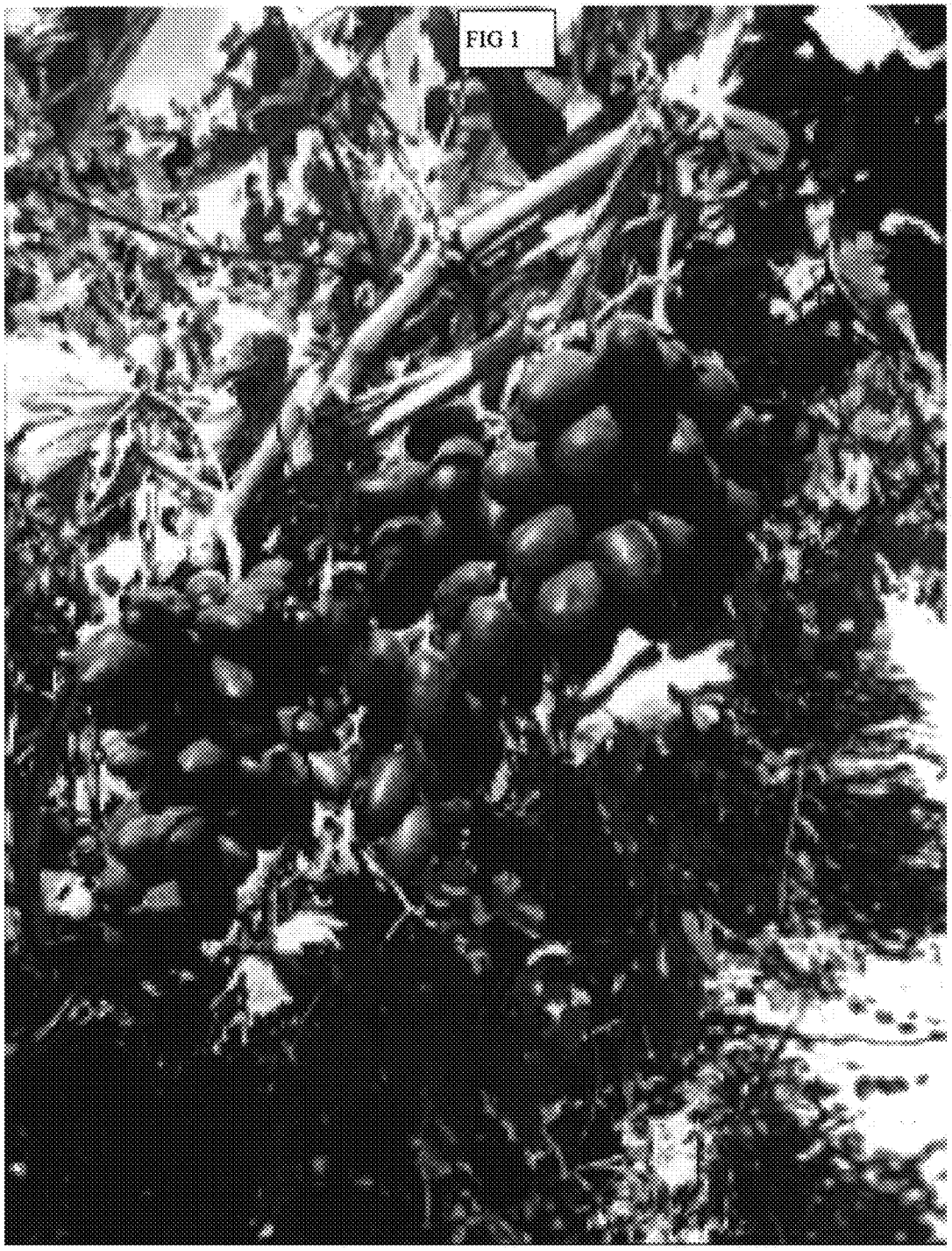
FIG. 1 Natural fruit clusters on seedling vine, 2012.
Figure 2:
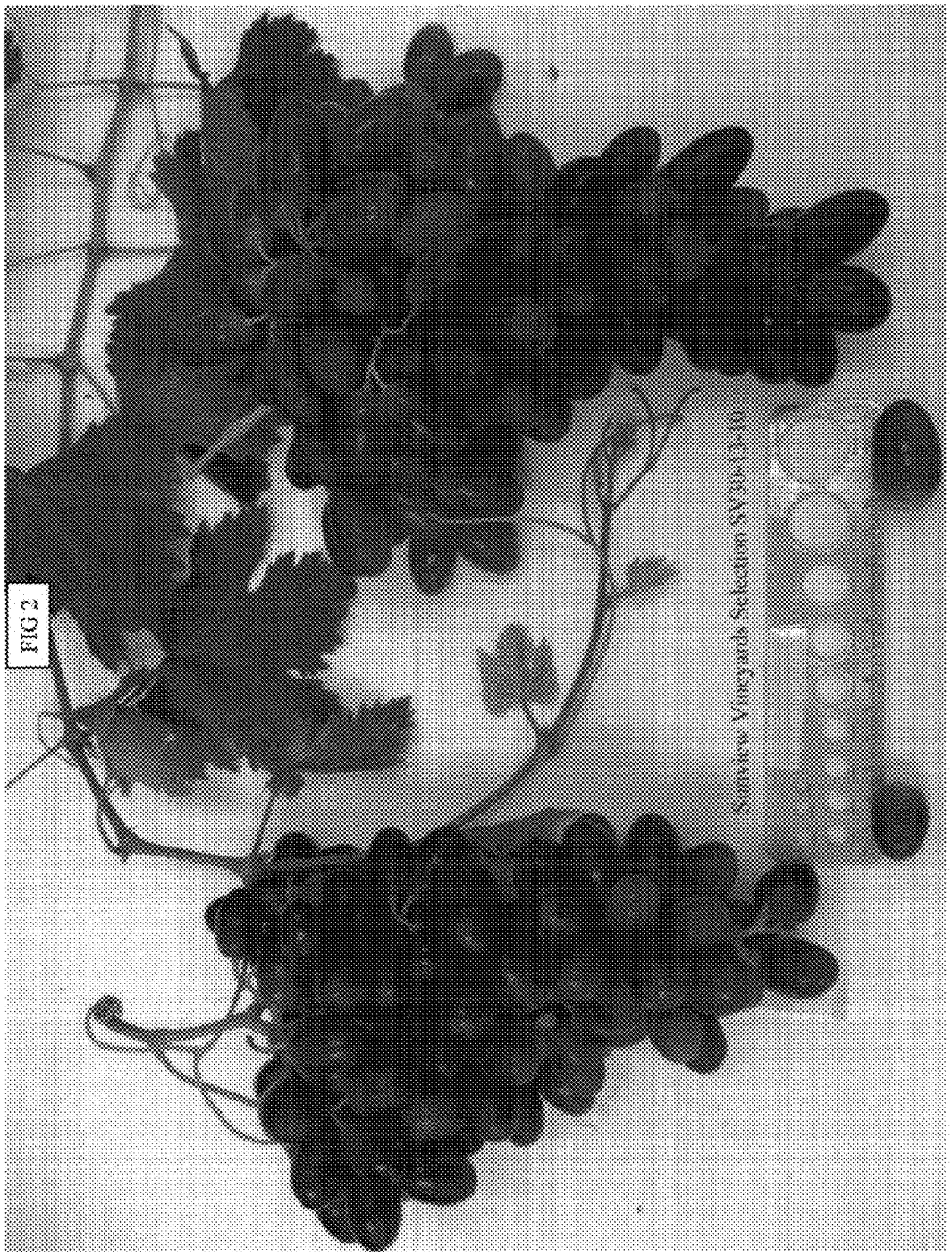
FIG. 2 Natural fruit cluster and cluster sprayed with gibberellic acid with shoots, leaves, tendrils and shoot tip, 2018.

The following detailed description sets forth the distinctive characteristics of grapevine named 'SV30-13-10'. Descriptions of the new invention apply to vines of grapevine named 'SV30-13-10' grown on 'Freedom' (unpatented) rootstock at a density of 1,537 vines per hectare grown near McFarland, Calif. in 2018. These vines were in their fourth year of full production, having been planted in 2013. These descriptions are believed to apply generally to the new variety grown under similar circumstances elsewhere. References to color correspond to The Royal Horticultural Society's Colour Chart, The Royal Horticultural Society, London, United Kingdom. Descriptors used herein conform to those set forth by the International Board for Plant Genetic Resources Institute Grape Descriptors (*Vitis* spp.) of 1983 and/or 1997 which were developed in collaboration with the Office Interantional de la Vigne et du Vin (OIV) and the International Union for the Protection of New Varieties of Plants (UPOV) and published in *Descriptors for Grapevine* (*Vitis spp.*) (Anonymous, International Plant Genetic Resources Institute, 1997, ISBN 92-9043-352-3).

Classification:

*Family*.—Vitaceae.
*Botanical name*.—*Vitis vinifera*.
*Variety name*.—'SV30-13-10'.

Plant:

*Vigor*.—Medium; vines spur-pruned and shoot thinned to 32 shoots.
*Density of foliage*.—Moderate.
*Productivity*.—Very productive when spur pruned, up to 32,000 kg/hectare.
*Hardiness*.—Hardiness observed to 0° C.
*Rootstock*.—'Freedom' (unpatented).

Trunk:

*Shape*.—Broadly elliptical.
*Straps*.—Long, split.
*Surface texture*.—Shaggy.

Young shoot:

*Form of tip*.—Fully open.
*Shoot tip color*.—Yellow Green Group 144B.
*Anthocyanin coloration of tip*.—Absent.
*Young shoot density of prostrate hairs at tip*.—Medium.
*Young shoot density of erect hairs at tip*.—Absent.
*Color of upper surface of shoot*.—Yellow Green Group 144A with streaks of Red Purple Group 64A.
*Color of lower surface of shoot*.—Yellow Green Group 145A.

Young leaves:

*Leaf color*.—Yellow Green Group 144B with anthocyanins present, Red Purple Group 61B.
*Density of prostrate hair between veins*.—Absent.
*Density of erect hairs between veins*.—Absent.
*Density of prostrate hairs on main veins*.—Sparse.
*Density of erect hairs on main veins*.—Medium, restricted to the base of main veins.

Mature leaves:

*Average blade length*.—12.1 cm.
*Average blade width*.—15.8 cm.
*Size of blade*.—Large.
*Shape*.—Pentagonal.
*Anthocyanin coloration of main veins on the upper side of the blade*.—Slight, at base of main veins on leaves exposed to the sun.
*Mature leaf profile*.—Undulating, cupped upwards and flattened within plane of blade.
*Blistering* (*upper surface*).—Absent.
*Leaf blade tip*.—In plane of blade.
*Margins*.—Lobed, serrated, undulating.
*Apex*.—Narrowly acute.
*Bases*.—Sagittate.
*Thickness*.—Medium.
*Undulation of blade between main and lateral veins*.—Slight.
*Shape of teeth*.—Broadly conical, both sides convex.
*Length of teeth*.—5-9 mm.
*Ratio length/width of teeth*.—About 1:1.
*General shape of petiole sinus*.—Half open.
*Tooth at petiole sinus*.—Absent.
*Petiole sinus limited by veins*.—Absent.
*Shape of upper lateral sinus*.—Closed.
*Prostrate hairs between veins* (*lower surface*).—Absent.
*Erect hairs between veins* (*lower surface*).—Absent.
*Prostrate hairs on main veins* (*lower surface*).—Absent.
*Density of erect hairs on main veins* (*lower surface*).—Moderate, limited to junctions of main veins.
*Prostrate hairs on main veins* (*upper surface*).—Absent.
*Upper surface*.—Summer color: RHS Green group 137B. Surface texture: Smooth. Surface appearance: Dull. Goffering of blade: Absent.
*Lower surface*.—Summer color: RHS Green group 143A. Anthocyanin coloration of main veins on lower leaf surface: Slight, at base of main veins on sun exposed leaves. Anthocyanin coloration on lateral veins: No. Glossiness: Low. Pubescence: Absent. Surface texture: Rough. Surface appearance: Dull.
*Petiole*.—Length: 8.8 cm. Length of petiole compared to middle vein: Slightly shorter. Density of prostrate hairs: Absent. Density of erect hairs: Absent. Shape of base of petiole sinus: Half open. Color: RHS Yellow green group 144B.

Tendrils:

*Color*.—RHS Yellow green group 144C.
*Length*.—15-20 cm.
*Branching*.—Bifurcated or trifurcated.
*Number of consecutive tendrils*.—Up to four.

Woody shoot:

*Woody shoot color*.—Greyed Orange Group 165B.

*Woody shoot surface*.—Smooth.

*Dormant bud color*.—Greyed Orange Group 175C.

Flowers:

*Flower sex*.—Perfect.

*Position of first flowering nodes*.—Usually on node 4.

*Number of inflorescences per shoot*.—One or two on nodes 4 and 5.

*Date of full bloom*.—May 11$^{th}$.

Fruit:

*Ripening period*.—Mid-season.

*Date of ripening*.—August 13th at McFarland, Calif.

*Particular flavor*.—Neutral *Vitis vinifera*.

*Use*.—Fresh market.

*Keeping quality*.—Good.

*Shipping quality*.—Good.

*Solids-sugar*.—20 brix at full maturity.

*Refractometer test*.—20.0 brix.

*Cluster*.—Bunch size: Large. Length (peduncle excluded): About 27 cm. Width: About 12.5 cm.

*Weight*.—Natural, without gibberellic acid treatment: About 828 g. Density: Well-filled. Number of berries: 96. Form: Conical (pyramidal) with occasional prominent shoulder.

*Pedicel*.—Color: Yellow Green Group 144B. Length: About 7-14 mm.

*Peduncle*.—Length: About 5 cm. Lignification: Slight. Color: RHS Yellow green group 144C.

*Berry*.—Size: Large. Uniformity of size: Uniform. Weight: Natural, without gibberellic acid treatment: About 7.1 g. Shape: Ovate. Presence of seeds: Seedless; most berries with soft remnants up to 5 mm in length. Cross section: Circular. Dimensions: Longitudinal axis: About 2.7 cm. Horizontal axis: About 1.8 cm. Skin color (without bloom): RHS Red Purple Group 60A to Black Group 202A where exposed to direct sunlight. Juiciness of flesh: Very juicy. Berry firmness: Very firm. Particular flavor: Neutral, typical *vinifera*. Bloom (cuticular wax): Wax is transparent; no translucent bloom. Pedicel length: About 7-14 mm. Berry separation from pedicel: Difficult. Skin thickness: Medium. Texture: Tender. Reticulation: Absent. Roughness: Absent. Tenacity: Tenacious to flesh. Tendency to crack: Resistant.

Disease and insect resistance: Moderately susceptible to powdery mildew which may be controlled with standard fungicides in California.

Having thus described and illustrated our new variety of grapevine, I claim:

1. A new and distinct variety of grapevine plant named 'SV30-13-10', substantially as illustrated and described herein.

* * * * *